(12) United States Patent
Ussembayev (10) Patent No.: US 9,551,648 B2
(45) Date of Patent: Jan. 24, 2017

(54) SUBSTRATE FOR THE GENERATION OF SURFACE PLASMONS AND SURFACE PLASMON POLARITONS BY MEANS OF AN EXCITATION RADIATION, METHOD FOR THE PRODUCTION OF THE SUBSTRATE, AND USES OF THE SUBSTRATE

(71) Applicant: Yerzhan Ussembayev, Delft (NL)

(72) Inventor: Yerzhan Ussembayev, Delft (NL)

( * ) Notice: Subject to any disclaimer, the term of this patent is extended or adjusted under 35 U.S.C. 154(b) by 251 days.

(21) Appl. No.: 14/455,228

(22) Filed: Aug. 8, 2014

(65) Prior Publication Data

US 2015/0042990 A1   Feb. 12, 2015

(30) Foreign Application Priority Data

Aug. 8, 2013   (DE) .................. 10 2013 108 584

(51) Int. Cl.
| | |
|---|---|
| *G01J 3/44* | (2006.01) |
| *G01N 21/03* | (2006.01) |
| *G01N 21/55* | (2014.01) |
| *G01N 21/552* | (2014.01) |
| *G01N 21/65* | (2006.01) |
| *B82Y 15/00* | (2011.01) |

(Continued)

(52) U.S. Cl.
CPC ............... *G01N 21/03* (2013.01); *B82Y 15/00* (2013.01); *G01N 21/55* (2013.01); *G01N 21/554* (2013.01); *G01N 21/658* (2013.01); *G03F 7/00* (2013.01); *B82Y 20/00* (2013.01); *G01N 2021/651* (2013.01)

(58) Field of Classification Search
CPC ...... G01N 21/03; G01N 21/55; G01N 21/658; G01N 2021/651; G01J 3/44

USPC ......................................... 356/301, 244, 445
See application file for complete search history.

(56) References Cited

U.S. PATENT DOCUMENTS

| | | | |
|---|---|---|---|
| 8,415,611 B2 | 4/2013 | Amako | |
| 2008/0218761 A1 | 9/2008 | Nishikawa | |

(Continued)

FOREIGN PATENT DOCUMENTS

EP   0442002 A1   8/1991

OTHER PUBLICATIONS

A-P. Blanchard-Dionne, et al, Intensity based surface plasmon resonance sensor using a nanohole rectangular array, Optics Express, Aug. 1, 2011, pp. 15041-15046, vol. 19, No. 16.

(Continued)

*Primary Examiner* — Abdullahi Nur
(74) *Attorney, Agent, or Firm* — Patentbar International, P.C.

(57) ABSTRACT

The invention is directed to a substrate for generating surface plasmons (SPs) and surface plasmon polaritons (SPPs) by means of an excitation radiation, wherein the substrate has a carrier layer and a coating with gold or silver. A surface of the carrier layer is provided with identical surface structures arranged in an array of rows and columns. The surface structures are recesses with an elongate shape which are arranged with a first periodicity ($P_H$) and with a second periodicity ($P_V$) in direction of the rows and orthogonal to the direction of the rows, respectively. The invention is further directed to a method for the production of the substrate and to uses of the substrate.

21 Claims, 5 Drawing Sheets

(51) Int. Cl.
*G03F 7/00* (2006.01)
*B82Y 20/00* (2011.01)

(56) References Cited

U.S. PATENT DOCUMENTS

| | | | |
|---|---|---|---|
| 2010/0017922 A1* | 1/2010 | Shin | B82Y 20/00 850/21 |
| 2010/0091274 A1* | 4/2010 | Bratkovski | G01N 21/658 356/301 |
| 2012/0182550 A1* | 7/2012 | Tang | G01N 21/7743 356/301 |

OTHER PUBLICATIONS

Xuan Dou, et al, Surface plasmon resonance and surface-enhanced Raman scattering sensing enabled by digital versatile discs, Applied Physics Letters, Jan. 26, 2012, pp. 041116-1-4, vol. 100, No. 4.
Burkan Kaplan, et al, Tuning optical discs for plasmonic applications, Plasmonics, Jul. 4, 2009, pp. 237-243, vol. 4.
Jason M. Montgomery, et al, Theory and modeling of light interactions with metallic nanostructures, Journal of Physics Condensed Matter, Jul. 18, 2008, pp. 1-11, vol. 20, No. 323201.
Perney et al, Tuning localized plasmons in nanostructured substrates for surface-enhanced Raman scattering, Optics Express, Jan. 23, 2006, pp. 847-857, vol. 14, No. 2.
Kocabas et al, Plasmonic band gap structures for surface-enhanced Raman scattering, Optics Express, Aug. 18, 2008, pp. 12469-12477, vol. 16, No. 17.
Baumgart et al, Off-resonance plasmonic enhanced femtosecond laser optoporation and transfection of cancer cells, Biomaterials, 2012, pp. 2345-2350, vol. 33.
Barnes et al, Surface plasmon subwavelength optics, Nature, Aug. 14, 2003, pp. 824-830, vol. 424, Nature Publishing Group.
Singh et al, Surface plasmon resonance enhanced transmission of light through gold-coated diffraction gratings, Analytical Chemistry, May 15, 2008, pp. 3803-3810, vol. 80, No. 10.
Tosello et al, Replication and dimensional quality control of industrial nanoscale surfaces using calibrated AFM measurements and SEM image processing, CIRP Annals—Manufacturing Technology, 2010, pp. 563-568, vol. 59.
Zayats et al, Nano-optics of surface plasmon polaritons, Physics Reports, 2005, pp. 131-314, vol. 408.

* cited by examiner

SUBSTRATE FOR THE GENERATION OF SURFACE PLASMONS AND SURFACE PLASMON POLARITONS BY MEANS OF AN EXCITATION RADIATION, METHOD FOR THE PRODUCTION OF THE SUBSTRATE, AND USES OF THE SUBSTRATE

RELATED APPLICATIONS

This application claims priority to German Patent Application No. DE 10 2013 108 584 filed Aug. 8, 2013, which is incorporated herein by reference in its entirety.

FIELD OF THE INVENTION

The invention is directed to a substrate which is suitable for the excitation of surface plasmons and surface plasmon polaritons by means of an excitation radiation. The invention is further directed to a method for producing the substrate and to uses of the substrate.

BACKGROUND OF THE INVENTION

In the relatively new technical field of plasmonics as a branch of nanophotonics, various efforts have been made in recent years to provide technical structures such as circuits in minimal area or to detect and analyze biological molecules or improve methods such as Raman spectroscopy or laser cell manipulation (e.g., Kocabas et al., Plasmonic Band Gap Structures for Surface-Enhanced Raman Scattering, *Optics Express* 16:12469-12477, 2008, and Baumgart et al., Off-Resonance Plasmonic Enhanced Femtosecond Laser Optoporation and Transfection of Cancer Cells, *Biomaterials* 33; 2345-2350, 2012).

A good overview of nanophotonic effects of surface plasmons, surface plasmon polaritons, photonic band gaps and the structuring of substrate surfaces is given in Barnes et al., Surface Plasmon Subwavelength Optics, *Nature* 424: 824-830, 2003, which is incorporated herein by reference.

In addition to a suitable excitation radiation, excitation of plasmons requires a structured, diffractive surface that is coated with a thin layer of gold or silver. Depending on the configuration of the structures on the surface, the achievable optical effects can be very finely tuned in coordination with the utilized excitation wavelength of excitation radiation. To obtain substrates with very fine structures, it has been suggested, for example, by Singh and Hillier, Surface Plasmon Resonance Enhanced Transmission of Light Through Gold-Coated Diffraction Gratings, *Analytical Chemistry* 80: 3803-3810, 2008, to use layers of writable DVDs (digital versatile discs). These layers of polycarbonate were provided with grooves with a spacing of about 1.5 μm and a height of about 160 nm and coated with gold. It was possible to use the substrate obtained in this way, for example, for detecting the thickness of ultrathin monolayers of alkanethiolates and antigen-antibody complex formation.

SUMMARY OF THE INVENTION

It is the object of the invention to provide a novel substrate by means of which surface plasmons and surface plasmon polaritons can be generated on the substrate in a predetermined manner.

This object is met by a substrate which is suitable for generating surface plasmons (hereinafter also called SP) and surface plasmon polaritons (hereinafter also called SPP) by means of an excitation radiation of a determined wavelength (excitation wavelength). The substrate is formed of a carrier (support) layer which is transparent for the excitation radiation and which has a surface structure on a surface of the carrier layer. The surface with the surface structure is coated with a coating of gold or silver that is reflective for the excitation radiation and suitable for generating SPPs through the excitation radiation. A substrate according to the invention is characterized in that the surface structure comprises a quantity of recesses (prolate nanowells or pits) of identical size which are separated from one another and which have in each instance a length in a longitudinal direction, a width in a transverse direction directed orthogonal to the longitudinal direction, and a depth.

The recesses are arranged in rows and columns in a regular two-dimensional arrangement (hereinafter also referred to as "array"), wherein the longitudinal directions of the recesses are directed parallel to one another and in direction of the rows. The columns run at an angle α to the rows. The array has a first periodicity of the surface structure in direction of the rows (hereinafter also called row direction) and a second periodicity of the surface structure orthogonal to the direction of the rows. The length of the recesses has a value in a range of from 100 to 2500 nm.

Viewed from the top, the recesses have an identical elongate shape with lateral lines extending parallel to one another in longitudinal direction, this elongate shape being limited at each end of the recess by a convex edge which is symmetrical to a center line of the recess extending in longitudinal direction. The clearance distance between the lateral lines extending parallel to one another is the width of the recess. The distance between the convex edges along the center line is the length of the recess. The depth is the distance from the surface with the surface structures to a base of the recess. The depth is preferably less than a thickness of the carrier layer.

The recesses are produced with the narrowest possible tolerances and in particular have pronounced "sharp-edged" transitions of the edges of the lateral lines and of the convex edges to the surface of the carrier layer.

The recesses are separated by separating portions of the surface, often also referred to as "lands", in which no surface structures are present.

The rows and columns present a two-dimensional arrangement or array. The rows and columns can run orthogonal to one another. The columns can also extend at an angle other than 90° relative to the rows as is the case with an array with a hexagonal arrangement of recesses. In such cases, the columns extend diagonally through the array. There is at least one row or at least one column in the array. Therefore, the array can also be formed, for example, only by a column and a quantity of rows.

Every column preferably contains at least one recess and a separating portion. The column width is given by the length of the recess and a length of the separating portion in row direction (first portion length). Each row preferably contains the recesses of this row and next to each recess a separating portion which extends orthogonal to the row direction and separates the recess from the next recess of an adjacent row, the length of this separating portion being measured orthogonal to the row direction. The row width is given by the width of the recess and a length of the separating portion orthogonal to the row direction (second portion length). Associated with the respective outermost rows and columns which have in each instance only one adjacent row or column, respectively, is a portion of the surface corresponding to the first portion length and second portion length, respectively, of the other rows and columns of the array.

By "first periodicity" is meant that distance in direction of the rows after which a pattern is repeated in a row. In the present description, the first periodicity is understood to mean the sum of the length of the recess and a portion length in row direction (column width). By "second periodicity" is meant a sum of the width of the recess and a portion length orthogonal to the row direction (row width). Therefore, the second periodicity corresponds to the row width. The surface structures, recesses and separating portions are arranged periodically in the array.

The coating has a material thickness of 20 to 55 nm, for example. Corresponding to the coating applied on the carrier layer in an embodiment of the substrate according to the invention, the substrate according to the invention has different characteristics, particularly with excitation of SPs and with a propagation of SPPs which possibly takes place. The coating is formed by nanoparticles of the utilized material and is applied to the carrier layer by means of suitable methods which are known to the person skilled in the art. The coating is preferably applied by means of a sputter method such as is used in the production of optical data storage media such as DVDs, HD-DVDs or Blu-Ray discs.

The carrier layer is preferably formed of polycarbonate (PC). PC has good optical characteristics when used for generating SPs and SPPs, such as high transparency, negligible light absorption, no (negligible) impurities in the material, good mechanical stability and minimum water absorption compared to other polymers. Further, PC is very good for high-precision production methods such as compression molding (see, e.g., Tosello et al., Replication and Dimensional Quality Control of Industrial Nanoscale Surfaces Using Calibrated AFM Measurements and SEM Image Processing, *CIRP Annals—Manufacturing Technology* 59: 563-568, 2010).

The array can have a rectangular shape. In this case, the rows and columns are oriented orthogonal to one another. In further embodiments of the array, angle α can be different than 90°, for example, 15°, 30°, 45°, 60° or 75°. Depending upon which (virtual) reference line, e.g., center line, lateral line, virtual row edges or column edges, etc., is selected for measuring angle alpha, this angle can be greater than 180° and can result in negative sine values, in which case the absolute value of angle α is used.

If angle α differs from 90°, the array has a hexagonal shape (honeycomb structure).

Broadly speaking, two different types of surface plasmons can be excited depending on the geometry of the recesses. For example, if the excitation radiation formed by electromagnetic waves illuminates the coating of a noble metal such as gold or silver, collective coherent oscillations of free electrons are excited at the metal surface. These oscillations of electrons cause a charge separation resulting in coherent dipole oscillations called surface plasmons (SPs).

At certain frequencies of excitation radiation exhibiting specific resonant frequencies of the SPs, the SPs in a nanoparticle can achieve maximal amplitude. An extensive enhancement of an initially present electromagnetic field is achieved by the maximal amplitude of this kind.

The excited electrons of a planar metal-dielectric arrangement (substrate) behave otherwise. In these substrates, the coherent dipole oscillations are not confined to the nanoscale recesses (nanostrucuture) but rather propagate along the metallic surface. These propagating plasmons are called surface plasmon polaritons (SPPs). Solving Maxwell's equation for a metal-dielectric arrangement (interface) described above gives a distribution function (dispersion relation) from which it clearly follows that the SPPs are damped waves (evanescent waves) which cannot be coupled directly into the propagating light of the laser by reason of the momentum conservation law.

Various techniques for compensation of momentum mismatch and for exciting SPPs are known (Zayats et al., Nanooptics of Surface Plasmon Polaritons, *Physics Reports* 408: 131-314, 2005).

In a preferred construction of the substrate according to the invention, the length of the recess is an integral multiple of the wavelength of a surface plasmon polariton (SPP) brought about by an excitation radiation of a determined wavelength. In an extremely advantageous manner, this type of configuration causes the entire recess to behave like a Fabry-Perot resonator. In this case, the excited SPPs cannot propagate along the interface (surface) between the coating (metal) and a surrounding dielectric medium such as air, water, acetone, ethanol, various polymers, oxides, or crystals such as $Al_2O_3$. However, it is possible in principle to use any dielectric. Standing SPs of this type are referred to as standing Bloch surface plasmon polaritons (BSPPs). It is especially noteworthy that the near-field enhancement can reach a value of 23. The BSPPs are coupled with the SPs excited at the recess and can form modes at the latter. In this way, the local electrical field is concentrated in the recess and losses caused through partial absorption of the excitation radiation in the metal of the coating are reduced, while the SPPs are accompanied by a higher dissipation of energy due to their propagation along the metallic surface of the substrate.

Another effect of the substrate according to the invention is the possibility of forming so-called surface plasmon band gaps, referred to hereinafter for the sake of brevity as band gaps. At many frequencies (range between ω− [lower band gap edge] and ω+ [upper band gap edge]; see Barnes et al., Surface Plasmon Subwavelength Optics, *Nature* 424, p. 827, Box 3, 2003) of the excitation radiation, it is not possible to couple the excitation radiation into SPPs on periodically structured substrates using momentum compensation approaches.

Structures (gratings) such as the substrate according to the invention are also known as surface plasmon polaritonic crystals by analogy to photonic crystals.

When the passing diffraction moment impinges on the lower band gap edge ω− at the lowest frequency of the band gap, the resulting dipole-dipole separations at frequencies of the band gap can be localized by means of the recesses. At frequencies outside the band gap, it is possible for the excited SPPs to propagate over the separating portions (space or lands) between the recesses (nanowells).

In another advantageous embodiment of the substrate according to the invention, a quantity of arrays can be provided on the substrate. The arrays can be identical. For example, a quantity of identical arrays is produced on a substrate and can be singulated subsequently by dividing the substrate. Naturally, different arrays can also be provided and then singulated Improved utilization of the surface area of the carrier layer can be accomplished in this way, for example. By specifically combining arrays of different characteristics, e.g., different first periodicities and second periodicities, lengths of recesses and material thicknesses of the coating, and through the specific arrangement and orientation of the arrays relative to one another, functional units such as optical circuits or optical channels can be provided on the substrate according to the invention.

The substrate according to the invention can be used in a variety of ways. For example, it can be used for Raman spectroscopy, surface-enhanced Raman spectroscopy (SERS), laser-based cell manipulation, e.g., transfection in tumor cells and/or stem cells, plasmonic waveguiding of optical telecommunication signals, controlled manipulation of cells, for example, cell membrane ion channels in neuron living cells, and for generating optical tweezers (single-beam gradient force traps).

The above-stated object is further met in a method for the production of a substrate according to the invention, wherein the carrier layer is supplied in a first method step of the method, and the surface structure is incorporated in the surface of a side of the carrier layer and the surface with the surface structure is then provided with a coating in a further method step. A method according to the invention is characterized in that the first periodicity is selected between 100 and 600 nm for applications of the substrate with an excitation radiation having a wavelength in the visible wavelength range (400-700 nm) or in the near infrared range (>700-1064 nm). Alternatively, the first periodicity is selected between 600 and 800 nm when the substrate is used for applications in which SPs and SPPs are to be excited with excitation radiations having excitation wavelengths selected from a range of from 1300 to 1550 nm for optical telecommunications purposes.

For both alternatives, the second periodicity is calculated on the basis of a calculation rule incorporating the length and width of one of the recesses and the first periodicity.

When excitation radiations with wavelengths selected from a range of from 1300 to 1550 nm are used for optical telecommunications purposes, zero dispersion can be achieved in optical fibers in an advantageous manner.

Compression molding, lithography, electron beam lithography, focused ion beam lithography or 2-photon polymerization, for example, can be used to introduce the surface structure.

The equation: second periodicity=length of the recess+ first periodicity−width of the recess, for example, can be used as calculation rule.

The choice of first periodicity is far more important than the choice of second periodicity for implementing the substrate according to the invention. When the substrate is illuminated with an excitation radiation at an illumination angle (of oblique incidence), the direction of the excitation radiation can be described through a k-wave vector lying in an illumination plane (plane of incidence). A magnetic field plane is orthogonal to the illumination plane and the k-wave vector, and an electric field plane is orthogonal to the magnetic field plane and the k-wave vector and lies within the illumination plane. The excitation radiation is p-polarized (TM-polarized [transversal-magnetic polarized]) wherein the magnetic field component is normal to the illumination plane.

The excitation radiation can be directed to the surface structures at illumination angles of from 0 to 90° along the k-vector. The excitation radiation is polarized at right angles to the length of the recesses. The k-vector of the excitation radiation is preferably oriented at right angles to the row direction.

An advantageous embodiment of the method according to the invention consists in that the length of the recess is selected as an integral multiple of the wavelength of a SPP caused by an excitation radiation with a determined wavelength so that BSPPs can be generated as was described above.

SPs can be excited at the sharp edges and corners of the recesses through excitation radiation over all of the excitation wavelengths and over all of the illumination angles. In addition, a near-field enhancement can be substantially improved when the SPs are coupled with the SPPs and the $n^{th}$-order of diffracted light of the excitation radiation compensates the SPP momentum mismatch.

Before beginning the actual production of the substrate according to the invention, it is advantageous to determine the wavelength of the SPPs before introducing the surface structure by means of a numerical simulation of an excitation with at least one excitation radiation and taking into account the optical characteristics of the substrate and to ascertain at least the first periodicity, the length of the recess and the material thickness of the coating corresponding to the results of the simulation. Of course, additional parameters can be determined in the simulation. The simulation is preferably carried out taking into account the totality of the substrate according to the invention, the excitation radiation and other relevant constraints. In so doing, it is possible to factor into the simulation observations and data gained from previous simulations. Further, observations about the degree to which simulations conform to produced substrates can be acquired by comparing simulated optical characteristics with optical characteristics actually observed in previously simulated, produced substrates and these observations can be incorporated in future simulations.

In an extremely advantageous manner, the method according to the invention allows an intermediate product generated from the manufacture of physical (optical) data storage media such as CDs (compact discs), DVDs (digital video discs), HD-DVDs (high-density versatile video discs) or Blu-ray discs to be used as carrier layer. The technology for producing such data storage media is well known.

It is possible to reuse (recycle) previously produced physical (optical) data storage media in that the layers of the physical (optical) data storage media formed of multiple layers are separated from one another and the coating, for example, gold, is applied to a polycarbonate layer as carrier layer. Surface structures such as recesses have been introduced in the surface of a side of the carrier layer prior to coating.

HD-DVDs and Blu-ray discs as physical (optical) data storage media have track pitches (corresponding to the first periodicity, for example) of 400 nm for HD-DVDs and 320 nm for Blu-ray discs. The corresponding widths of the structures are 200-250 nm and 130 nm, respectively. It is possible in principle to excite SPPs at the structures of a (HD-)DVD with excitation radiation of an excitation wavelength in the infrared and mid-infrared range. These excited SPPs can be used in optical telecommunications systems based on directed waveguiding of surface plasmons (SP waveguiding).

The method according to the invention makes it possible to produce inexpensive substrates and even to make use of existing technologies for this purpose. Since HD-DVDs, for example, were only produced for a few years, the method for producing them is known and the required technical plants are still extant or can easily be provided again; however, there has largely been no use for this already obsolete technology. The method according to the invention also suggests a new technical application for the existing technology.

BRIEF DESCRIPTION OF THE DRAWINGS

The invention will be described more fully in the following with reference to illustrations and embodiment examples. The drawings show.

DETAILED DESCRIPTION OF THE PREFERRED EMBODIMENTS

Figure 1:
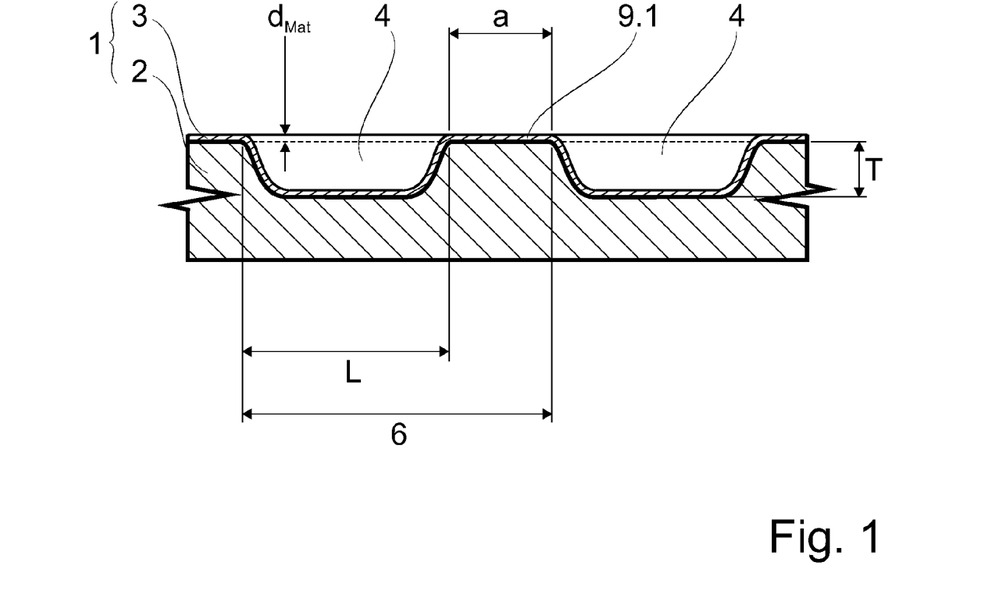
FIG. 1 is a first embodiment example of a substrate according to the invention in a side view of a section along a row.

FIG. 1 schematically shows a cross section through a substrate 1 according to the invention in which a coating 3 of gold having a material thickness $d_{Mat}$ of 25 nm is applied on a surface of a side of a carrier layer 2 of polycarbonate. The depicted section runs in direction of a row 5 (see FIG. 2) along a center line 7 (see also FIG. 2) of recesses 4 (nanowells) provided along the row 5. The recesses 4 have a length L and a depth T and represent surface structures of the surface of the carrier layer 2. The material thickness $d_{Mat}$ of the coating 3 is constant and completely covers the surface and surface structures, depth T being smaller than material thickness $d_{Mat}$. The recesses 4 are separated from one another by a separating portion of the surface in row direction (first separating portion in row direction 9.1) with a first portion length a. The width of a column 6 (see also FIG. 2) is given by the length L of a recess 4 and the first portion length a.

None of the elements in FIGS. 1 to 7 are drawn to scale and they are shown only schematically.

Figure 2:
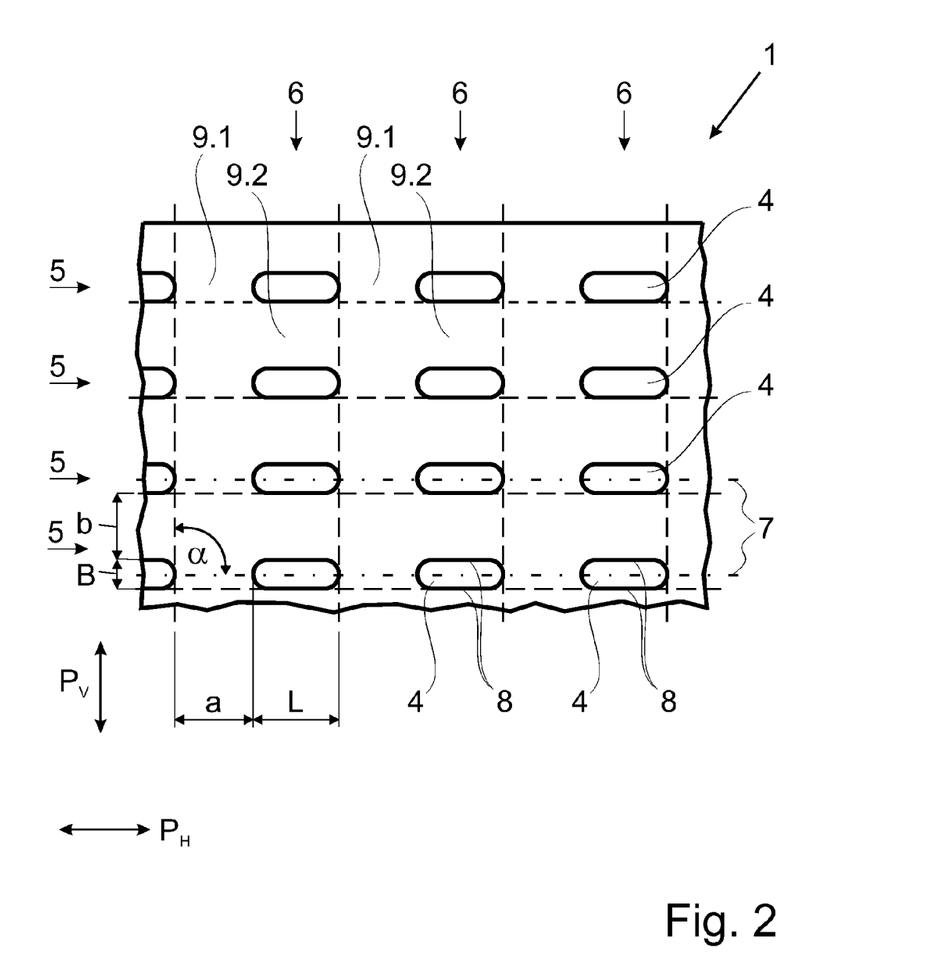
FIG. 2 is a first embodiment example of a substrate according to the invention with a rectangular array (detail)
Figure 3:
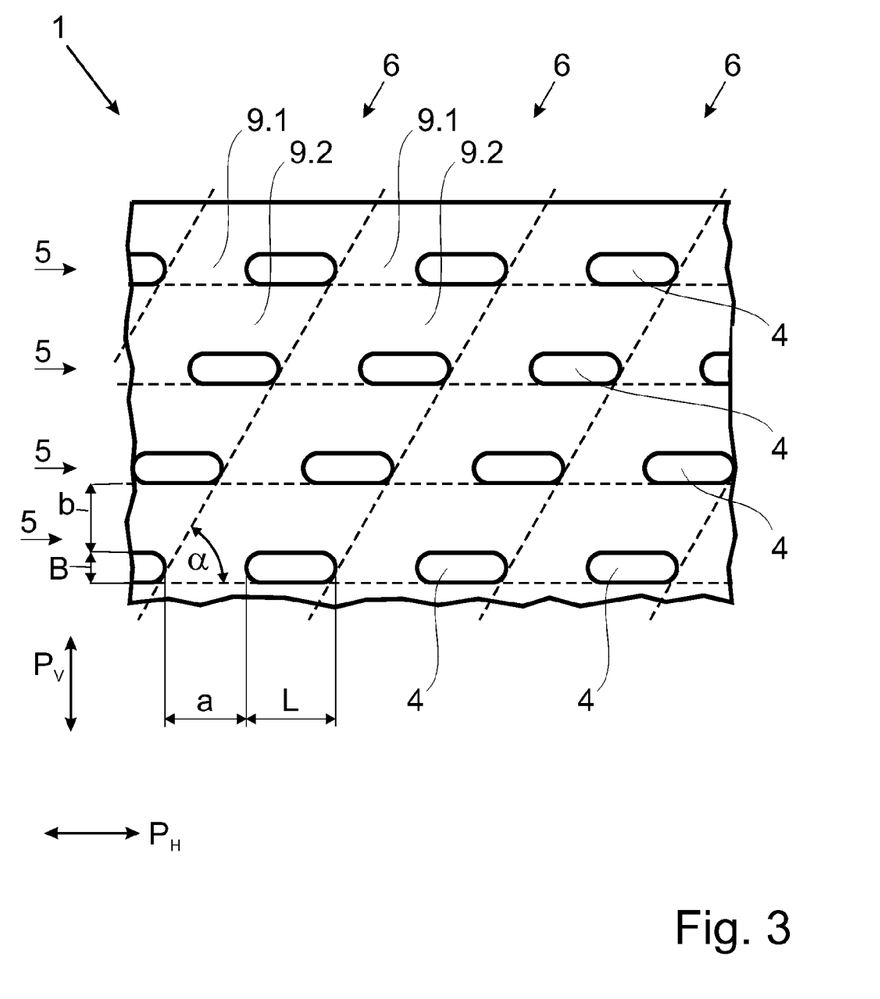
FIG. 3 is a second embodiment example of a substrate according to the invention with a hexagonal array (detail)

FIG. 2 shows a two-dimensional arrangement of identical recesses 4 in the form of an array with rows 5 extending parallel to one another and with columns 6 extending parallel to one another. The rows 5 and columns 6 extend at right angles to one another. In each row 5, the recesses 4 are oriented along a common center line 7 (only two of which are shown) so that the longitudinal directions of the recesses 4 are directed toward the rows 5. Every recess 4 has, viewed from above, two lateral lines 8 which extend parallel to one another and which are spaced apart from one another by a width B. The individual recesses 4 are separated from one another in direction of rows 5 by the first separating portion in row direction 9.1 (only two of which are shown) having the first portion length a. The rows 5 have a row width given by the sum of width B and a second portion length b of a second separating portion in column direction 9.2. The rows 5 are shown bounded by virtual dashed lines which extend in each instance along a lateral line 8, in this case the lateral line 8 at the bottom of the drawing. Regular repetition of the sequence: length L of recess 4—first separating portion in row direction 9.1 gives a column width and a first periodicity $P_H$ in row direction. In this first embodiment example, the first periodicity $P_H$ is illustrated by columns 6.

Regular repetition of the sequence: width B of recess 4—second separating portion in column direction 9.2 gives a row width and a second periodicity $P_V$ orthogonal to the row direction.

In an array according to the second embodiment example of substrate 1 (FIG. 3), angle α is 45°. Therefore, the columns extend diagonally through the array. The array has a hexagonal shape. The first periodicity $P_H$ is identical in all rows 5, but the recesses 4 are offset relative to one another in the individual rows 5 corresponding to the diagonal course of the columns 6. The second periodicity $P_V$ is also determined orthogonal to the row direction in this embodiment example.

By means of a numerical simulation, the optical characteristics of a substrate 1 according to the invention can be determined already before being produced.

Figure 4:
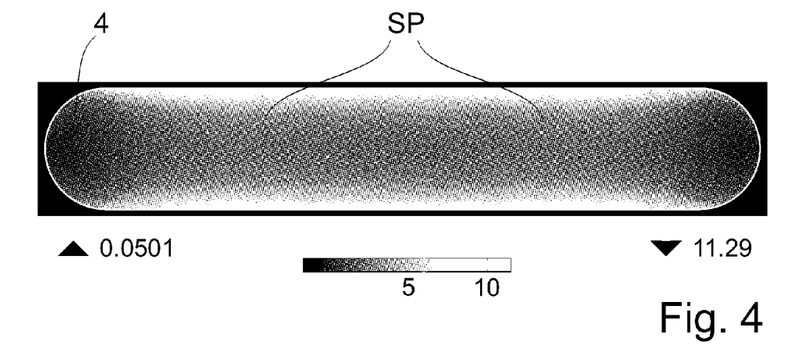
FIG. 4 is a schematic grayscale depiction of the energy (electric field) distribution at a recess with an excitation wavelength of 860 nm, an illumination angle of 0° and a length of 900 nm.

FIG. 4 shows a recess 4 having a length L of 900 nm. Recess 4 is illuminated by excitation radiation having an excitation wavelength of 860 nm at an illumination angle of 0° and SPs are excited at the sharp edges of the lateral lines 8. The field enhancement $|E_{max}|/|E_0|$ is 11.29. Bright areas have higher levels of energy than dark areas.

Figure 5:
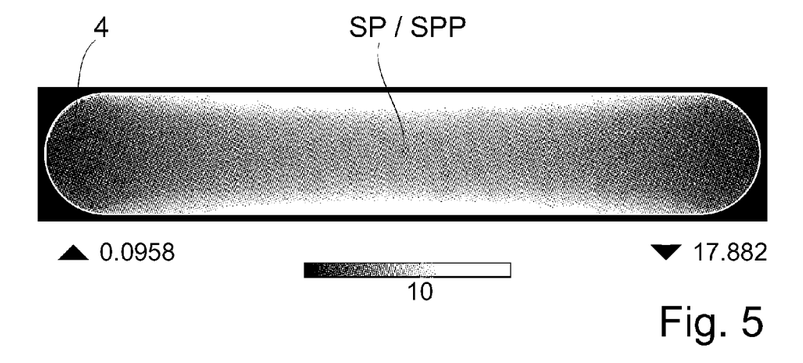
FIG. 5 is a schematic grayscale depiction of the energy (electric field) distribution at a recess with an excitation wavelength of 775 nm, an illumination angle of 0° and a length of 900 nm.

FIG. 5 shows another recess 4 having a length L of 900 nm. Recess 4 is illuminated by excitation radiation having an excitation wavelength of 775 nm at an illumination angle of 0° and SPs are excited at the sharp edges of the lateral lines 8. The field enhancement $|E_{max}|/|E_0|$ is 17.88. The excited SPs are coupled with the SPPs (the designated areas are shown only for illustrative purposes).

Figure 6:
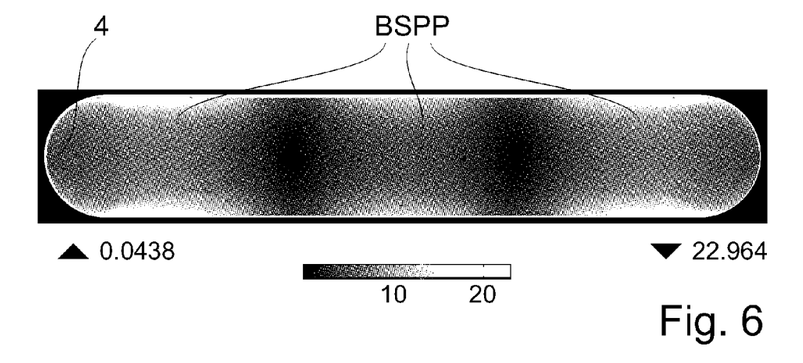
FIG. 6 is a schematic grayscale depiction of the energy (electric field) distribution at a recess with an excitation wavelength of 715 nm, an illumination angle of 0° and a length of 900 nm.

FIG. 6 shows another recess 4 having a length L of 900 nm. Recess 4 is illuminated by excitation radiation having an excitation wavelength of 715 nm at an illumination angle of 0°, and SPs are excited at the sharp edges of the lateral lines 8. The field enhancement $|E_{max}|/|E_0|$ is 23.96. In this example, length L is an integral multiple of the wavelength of the excited SPs. The recess 4 functions as a Fabry-Perot resonator and standing Bloch surface plasmon polaritons (BSPPs) are formed in the recess 4. Two nodes at which the energy is minimal 11.29 are visible in the middle of the recess 4.

Figure 7:
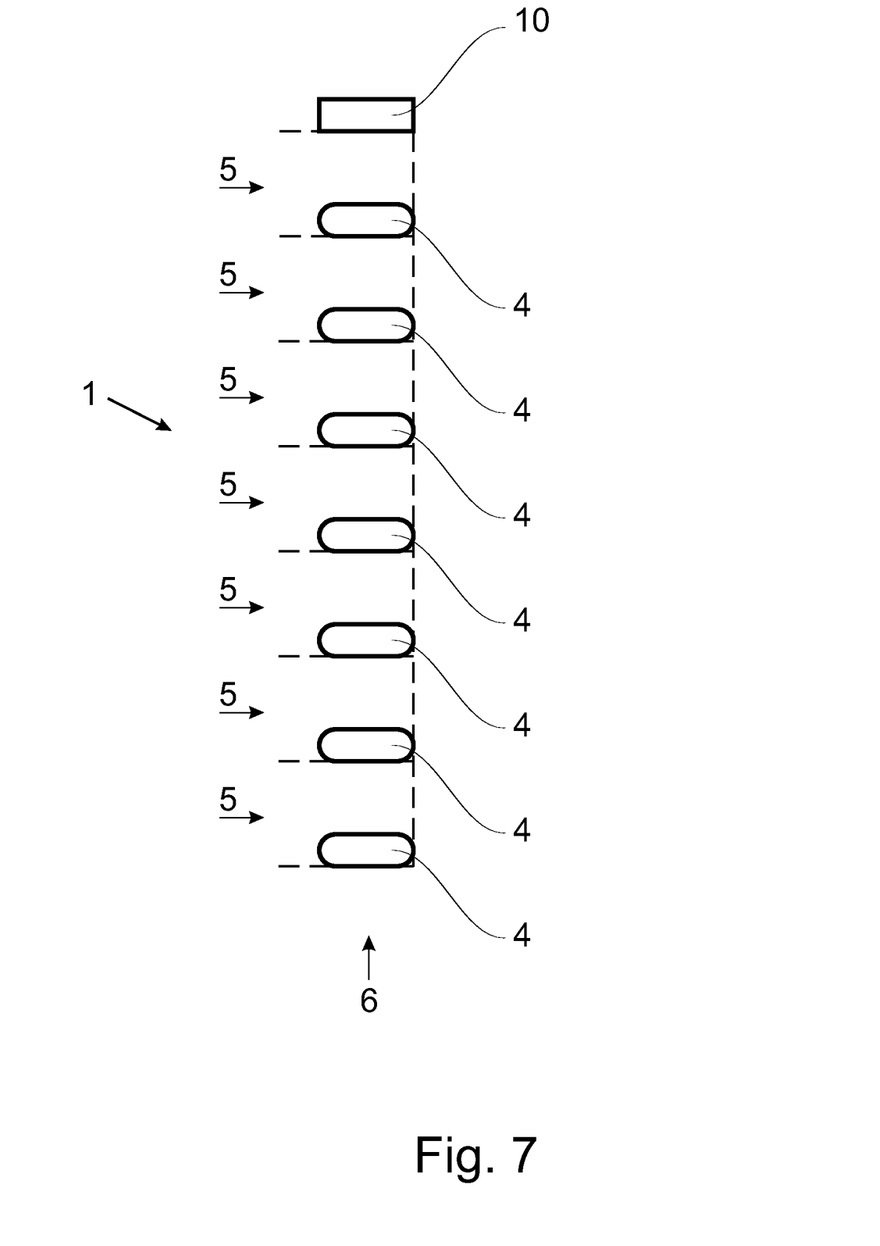
FIG. 7 is a schematic view of an array with only one column and a quantity of rows.

FIG. 7 shows a special shape of the array. The array is formed of a column 6 and a plurality of rows 5. A detection unit 10 in the form of a sensor is provided at one end of the column 6.

REFERENCE NUMERALS 1 substrate
2 carrier layer
3 coating
4 recess
5 row
6 column
7 center line
8 lateral line
9.1 first separating portion in row direction
9.2 second separating portion in column direction
10 detection unit
$P_H$ first periodicity
$P_V$ second periodicity
L length (of the recess 4)
B width (of the recess 4)

T depth (of the recess 4)
a first portion length
b second portion length
α angle
$d_{Mat}$ material thickness
SP surface plasmon
SPP surface plasmon polariton
BSPP Bloch surface plasmon polariton

What is claimed is:

1. A substrate for generating surface plasmons (SPs) and surface plasmon polaritons (SPPs) by excitation radiation of a determined wavelength, comprising:
   a carrier layer transparent to the excitation radiation comprising a surface structure on a surface of the carrier layer, and a metal coating on the surface structure, the coating being suitable for propagating SPPs excited by the excitation radiation; and
   the surface structure comprising a plurality of spaced apart prolate recesses of an identical size, each recess having a length (L) in a longitudinal direction selected from a range between 100 nm and 2500 nm, a width (B) in a transverse direction orthogonal to the longitudinal direction, and a depth (T), wherein each recess is elongated in the length L with respect to the width B;
   the plurality of the recesses being arranged in rows and columns of a two dimensional array, wherein longitudinal directions of the prolate recesses are parallel to one another and wherein the columns form an angle α relative to the rows, the array having a first periodicity ($P_H$) of the surface structure in direction of the rows and a second periodicity ($P_V$) of the surface structure in direction of the columns.

2. The substrate according to claim 1, wherein the carrier layer is made of polycarbonate.

3. The substrate according to claim 1, wherein the angle (of the array is 90° or 60°.

4. The substrate according to claim 1, wherein the length (L) of each recess is an integral multiple of a wavelength of a surface plasmon polariton (SPP) excited by the excitation radiation.

5. The substrate according to claim 1, a plurality of arrays is provided on the substrate.

6. The substrate of claim 1, wherein the first periodicity ($P_H$) is selected from a range between 100 nm and 600 nm and wherein the determined wavelength of the excitation radiation is selected from a range from 400 nm to 1064 nm.

7. The substrate of claim 1, wherein the first periodicity ($P_H$) is selected from a range between 600 nm and 800 nm and wherein the determined wavelengths of the excitation radiation is selected from a range from 1300 nm to 1550 nm.

8. The substrate of claim 1 wherein the second periodicity ($P_V$) is determined by a relationship between the length (L), width (B), and the first periodicity ($P_H$).

9. A method of producing a substrate for generating surface plasmons (SPs) and surface polaritons (SPPs) by excitation radiation of a determined wavelength, the method comprising:
   providing a carrier layer transparent to the excitation radiation comprising a surface structure on a surface of the carrier layer, and a metal coating on the surface structure, the coating being suitable for propagating SPPs excited by the excitation radiation;
   forming the surface structure to comprise a plurality of spaced apart prolate recesses of an identical size, each recess having a length (L) in a longitudinal direction selected from a range between 100 nm and 2500 nm, a width (B) in a transverse direction orthogonal to the longitudinal direction, and a depth (T), wherein each recess is elongated in the length L with respect to the width B; and
   forming the plurality of the recesses in rows and columns of a two-dimensional array, wherein longitudinal directions of the prolate recesses are parallel to one another, the array having a first periodicity ($P_H$) of the surface structure in direction of the rows and a second periodicity ($P_V$) of the surface structure orthogonal to the direction of the rows.

10. The method of claim 9, wherein the first periodicity ($P_H$) is selected from a range between 100 nm and 600 nm and wherein the determined wavelength of the excitation radiation is selected from a range from 400 nm to 1064 nm.

11. The method substrate of claim 9, wherein the first periodicity ($P_H$) is selected from a range between 600 nm and 800 nm and wherein the determined wavelengths of the excitation radiation is selected from a range from 1300 nm to 1550 nm.

12. The method substrate of claim 9, wherein the second periodicity ($P_V$) is determined by a relationship between the length (L), width (B), and the first periodicity ($P_H$).

13. The method according to claim 12, wherein the relationship is an equation: the second periodicity ($P_V$)=length (L)+first periodicity ($P_H$)−width (B).

14. The method according to claim 9, wherein the length (L) is selected as an integral multiple of a wavelength of the SPP excited by the excitation radiation with the determined wavelength to generate standing Bloch waves (BSPPs) in each recess.

15. The method according to claim 9, further comprising determining a wavelength of the SPPs before forming the surface structure by a numeric simulation of an excitation with at least one excitation radiation and with taking into account optical characteristics of the substrate and, derived from the results of the simulation, determining at least the first periodicity ($P_H$), the length (L) and a thickness ($d_{Mat}$) of the coating.

16. The method according to claim 9, wherein the carrier layer is an optical data storage medium.

17. The method according to claim 9, further comprising using the substrate for generating surface plasmons (SPs) and surface polaritons (SPPs) by the excitation radiation of the determined wavelength for Raman spectroscopy.

18. The method according to claim 9, further comprising using the substrate for generating surface plasmons (SPs) and surface polaritons (SPPs) by the excitation radiation of the determined wavelength for laser-based manipulation in tumor cells and/or stem cells.

19. The method according to claim 9, further comprising using the substrate for generating surface plasmons (SPs) and surface polaritons (SPPs) by the excitation radiation of the determined wavelength for plasmonic waveguiding of optical telecommunication signals.

20. The method according to claim 9, further comprising using the substrate for generating surface plasmons (SPs) and surface polaritons (SPPs) by the excitation radiation of the determined wavelength for a controlled manipulation of cells.

21. The method according to claim 9, further comprising using the substrate for generating surface plasmons (SPs) and surface polaritons (SPPs) by the excitation radiation of the determined wavelength for generating optical tweezers.

* * * * *